United States Patent [19]
Aleshin et al.

[11] Patent Number: 5,396,333
[45] Date of Patent: Mar. 7, 1995

[54] DEVICE AND METHOD FOR OBSERVING AND ANALYZING A STREAM OF MATERIAL

[75] Inventors: Stephen Aleshin, Cincinnati; Vanon D. Pratt, Hamilton, both of Ohio

[73] Assignee: General Electric Company, Cincinnati, Ohio

[21] Appl. No.: 886,566

[22] Filed: May 21, 1992

[51] Int. Cl.⁶ .................. G01B 11/04; B23K 26/02
[52] U.S. Cl. .................. 356/385; 219/121.83; 250/574; 356/340; 356/376; 356/386
[58] Field of Search .............. 356/376, 384, 385, 336, 356/338, 340, 330, 386, 441, 442; 250/574, 573; 219/121.83, 121.84; 358/107, 105

[56] References Cited

U.S. PATENT DOCUMENTS

| | | | |
|---|---|---|---|
| 3,096,767 | 7/1963 | Gresser et al. | 219/121.83 |
| 3,377,597 | 4/1968 | Muta | 346/33 |
| 3,478,597 | 11/1969 | Merigold et al. | 73/422 |
| 3,591,290 | 7/1971 | Zinner et al. | |
| 3,710,798 | 1/1973 | Bredemeier | 128/303.1 |
| 3,854,432 | 12/1974 | Dahneke | 73/28 |
| 4,205,384 | 5/1980 | Merz et al. | 364/555 |
| 4,318,180 | 3/1982 | Lundqvist et al. | 356/442 |
| 4,652,755 | 3/1987 | Solomon et al. | 356/441 |
| 4,660,971 | 4/1987 | Sage et al. | 356/39 |
| 4,724,299 | 2/1988 | Hammeke | 219/121.84 |
| 4,896,967 | 1/1990 | Douglas-Hamilton et al. | 356/442 |
| 4,896,967 | 1/1990 | Boisseau et al. | 356/442 |
| 4,918,284 | 4/1990 | Weisz | 219/121.83 |
| 4,937,445 | 6/1990 | Leong et al. | 250/237.6 |
| 4,990,795 | 2/1991 | Suzuki et al. | 250/574 |
| 5,095,386 | 3/1992 | Scheibengraber | 359/668 |

*Primary Examiner*—Jeffrey R. Snay
*Assistant Examiner*—Rachel Freed
*Attorney, Agent, or Firm*—Jerome C. Squillaro; Bernard E. Shay

[57] ABSTRACT

A device for observation and analysis of a cross-sectional portion of a stream of material, which may be either a particle or a fluid stream, includes a laser light source for generating a beam of light. A focusing lens is disposed in an optical path between the laser source and the stream and a plano-cylindrical lens of a selected focal length is disposed in the optical path between the focusing lens and the stream. The focusing lens and the plano-cylindrical lens convert the beam of light from the laser light source to a plane of light which may be projected through the stream to illuminate a selected cross-section of the stream for observation and analysis thereof.

24 Claims, 3 Drawing Sheets

# DEVICE AND METHOD FOR OBSERVING AND ANALYZING A STREAM OF MATERIAL

BACKGROUND OF THE INVENTION

The present invention relates to analysis and evaluation of a fluid or particle stream and more particularly to a device for observing and analyzing a powder stream from a coaxial powder feed nozzle of a laser welding apparatus to provide better control of laser welding parameters during a laser welding operation.

Laser welding apparatuses with coaxial powder feed nozzles are receiving wider application in industrial production environments, such as the manufacture of gas turbine engines and the like. An example of a laser apparatus with a coaxial powder feed nozzle is disclosed in U.S. Pat. No. 4,724,299, entitled "Laser Spray Nozzle and Method" issued on Feb. 9, 1988, to Hammeke.

To provide acceptable weld integrity, particularly in the gas turbine engine manufacturing industry, it is important that the powder is fed from the coaxial feed nozzle in a consistent uniform flow pattern to provide welds with minimal or no voids or other defects. Unacceptable weld joints can result because of nonuniform or asymmetrical distribution or shape of the powder stream exiting the coaxial powder feed nozzle.

In order to better understand and control the dynamics of the laser welding operation when using a coaxial feed nozzle, the ability to observe and analyze the powder stream exiting the nozzle including the interior portion of the stream is desirable.

A current method used to observe and analyze the powder stream is to direct a beam of white light of sufficient intensity on the powder stream so that the powder stream is clearly visible to the human eye. The gas flow rate of the carrier gas may then be adjusted until the visible powder stream shape or cone of the stream exhibits a desired shape which has proven to provide acceptable laser welding results. A disadvantage to this method, however, is that only the overall shape of the outer portion of the powder stream is discernable. The interior profile of the stream is masked by the reflection of the light from the outer portion of the powder stream cone. The shape or profile of the interior portion of the powder stream has been found to be of importance, if not more importance than the shape or profile of the exterior portion of the stream. This is because of the interaction between the laser beam and the powder stream during a welding process.

SUMMARY OF THE INVENTION

It is accordingly a primary object of the present invention to provide a novel device for observation and analysis of a powder stream which is not subject to the foregoing disadvantages.

It is another object of the present invention to provide a device for observation and analysis of the entire powder stream including the interior portion or profile.

It is a further object of the present invention to provide a device for generating a three-dimensional representation of the powder stream.

It is a further object of the present invention to provide a device for observation and analysis of a cross-sectional portion of a powder stream during a laser welding operation.

In accordance with the present invention, a device for observing and analyzing a particle or fluid stream of material includes a laser light source for generating a beam of light. A focusing lens is disposed in an optical path between the laser source and the powder stream and a plano-cylindrical lens of a selected focal length is disposed in the optical path between the focusing lens and the powder stream. The focusing lens and the plano-cylindrical lens convert the beam of light from the laser light source to a plane of light which may be projected through the powder stream to illuminate a selected cross-section of the powder stream for observation and analysis thereof. The laser light source is preferably of a visible wavelength, such as a helium neon laser or the like, so that the illuminated cross-section of the powder stream may be viewed by the human eye; although, other laser light sources may be used with a camera or other detector which can convert the illuminated powder stream cross-section to an image which can be viewed by the human eye.

The device of the present invention may also include a mechanical arrangement for moving the plane of light through the powder stream to illuminate a plurality of different cross-sections during which images are generated by a camera or the like to permit analysis of all portions of the powder stream. The camera may also be a video camera which may be connected to a vision computer for digitizing the video signals which may then be processed and stored. The stored video images may then be reconstructed to provide a three-dimensional representation of the powder stream.

In accordance with a further embodiment of the present invention, if it is desirable to observe and analyze a powder steam being deposited from a coaxial feed nozzle of a laser welding apparatus during a welding process, the powder stream observing and analyzing device will include a laser light source which operates at a different wavelength from the spectral emissions created during the welding process including the emissions from the laser source of the laser welding apparatus. The device will further include a camera or detector means for detecting the selected powder stream cross-section illuminated by the laser light source and will generate an image of the cross-section. Because the light source and the detector operate at the same wavelength, which is substantially different from the wavelengths of the spectral emissions created during processing and different from the emissions of the laser source of the welding apparatus during operation, it is possible to view and analyze the powder stream, including the interior portion, during a laser welding operation and to make whatever adjustments are necessary to improve the laser welding process.

These and other objects of the invention, together with features and advantages thereof, will become apparent from the following detailed specification when read with the accompanying drawings in which like reference numerals refer to like elements.

DETAILED DESCRIPTION OF THE PREFERRED EMBODIMENTS

Figure 1:
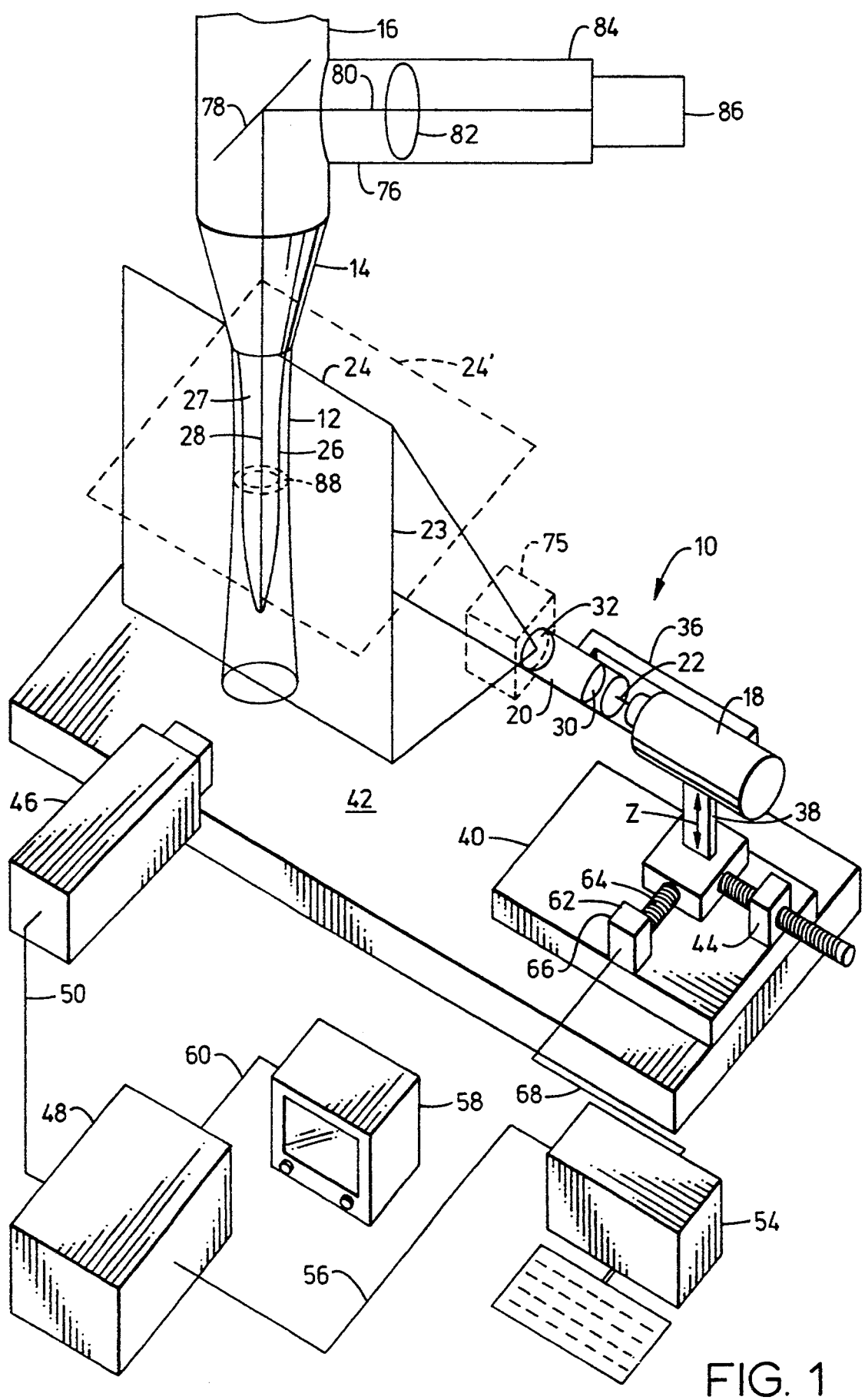
FIG. 1 is a perspective, schematic view of the powder stream analyzing device in accordance with the present invention.

Referring to FIG. 1, in accordance with the present invention, a device 10 for analyzing a powder stream 12, such as a powder stream from a coaxial feed nozzle 14 of a laser welding apparatus 16 or the like, includes a high intensity light source 18, preferably a diode laser light source, such as a 3 milliwatt TOLD9201 as manufactured by Toshiba or the like. A line generator means 20 is disposed between the light source 18 and the powder stream 12 to convert a beam of light 22 from the light source 18 to a line 23 of light which is actually the edge of a plane 24 of light. The plane 24 of light is projected through the powder stream 12 by the line generator means 20 to illuminate a selected cross-section 26 of the powder stream 12 for observation and analysis of the powder stream shape or profile, including the stream interior portion 27. By analyzing the shape of the powder stream, carrier gas flow rates and other parameters can be adjusted to control the shape or profile of the stream in response to the laser welding operation to be performed to provide optimum interaction between the welding laser beam 28 from the laser source (not shown) of welding apparatus 16 and the powder stream 12 to provide high quality welds with minimal voids or other defects.

The light source 18 is preferably a laser light source because a laser beam is less divergent and provides a more refined line 23 or plane 24 of light relative to other sources; however, any light source which adequately illuminates the powder stream selected cross-section 26 and highlights the interior portion 27 may be used. Additionally, the light source also preferably generates light within the visible spectrum which can be viewed by the human eye, although a detector or camera which can convert the illuminated, selected cross-section 26 to an image viewable by the human eye may be used as well.

The line generator means 20 includes a focusing lens 30 of a selected focal length and a plano-cylindrical lens 32 of a selected focal length. The laser light beam 22 enters the light line generator means 20 where both the focusing lens and the plano-cylindrical lens are adjustible relative to each other and to the light source 18 to convert the laser light beam 22 to the line of light 23 and to allow focusing of the line of light 23 at a predetermined focal point if viewed coaxially with the direction of propagation of the laser light beam 22.

The laser light source 18 and the line generator means 20 are preferably mounted with respect to one another by a bracket 36. The combination of the laser light source 18 and line generator 22 may then be mounted on an adjustable pedestal 38 which preferably sits upon an adjustable base 40. As will be evident to those skilled in the art, the device 10 is portable and may be moved from one laser welding apparatus 16 to another. The base 40 of device 10 allows the device 10 to be placed on the surface of a multi-axis table 42 usable with a laser welding apparatus. The powder stream observing and analyzing device 10 may be placed on the multi-axis table 42 and positioned by hand to provide the focused line 23 of light and plane 24 of light passing through the selected cross-section 26 of powder stream 12. A micrometer adjustment arrangement 44 may also be provided for fine adjustment and focusing of the light line 23 with respect to the powder stream 12.

A camera 46, such as a still photographic camera, video camera or similar device for detecting the illuminated powder stream cross-section 26 and generating an image thereof for analysis, is positioned so that the selected cross-section 16 of powder stream 12 is within the field of view of the detector or camera 46. Preferably, the camera 46 is positioned perpendicular to the light plane 24, although constraints of the operating environment may require viewing at some angle relative to the light plane 24. If camera 46 is a video camera, the camera 46 may be interconnected to a vision computer 48, such as an Intelledex Model No. 386HR, to digitize the video signals received by camera 46 for processing. Video camera 46 may be interconnected to the vision computer 48 by a suitable communications link 50. Vision computer 48 may be connected by another communications link 56 to a processing computer 54 for storing and processing the digitized images. Computer 54 may be a standard desktop PC type computer which is compatible with the vision computer 48 and has sufficient storage and computing capacity to perform any desired analysis or image reconstruction. A video monitor 58 may also be interconnected to the vision computer 48 by a suitable communications link 60. The monitor 58 permits observation and analysis of the powder-stream cross-section 26 on a real-time basis and also permits replay of the digitized and stored images of the powder stream cross-section 26.

In accordance with one embodiment of the present invention, the pedestal 38 supporting the laser light source 18 and the line generator means 20 may be connected to a positioning means 62, such as an advancing worm screw 64 and small electrical drive motor 66 for advancing the worm screw 64 and moving the laser light source 18 and line generator means 20 to cause the plane 24 of light to advance through the powder stream 12 to illuminate a plurality of different cross-sections 26 of the powder stream 12 to permit observation and analysis of substantially the entire powder stream 12, including the interior portion 27. Images of each of these different cross-sections 26 may be generated by the camera 46, digitized and stored for further analysis. The plurality of images may be further processed and reconstructed using computers 48 and 54 to provide a three-dimensional representation of the powder stream 12 which may be displayed on video monitor 58. Movement of the laser light source 18 and the line generator means 20 may be controlled by interconnecting the computer 54 with the positioning means 62 by a suitable communications link 68 to provide an automated system.

Figure 2:
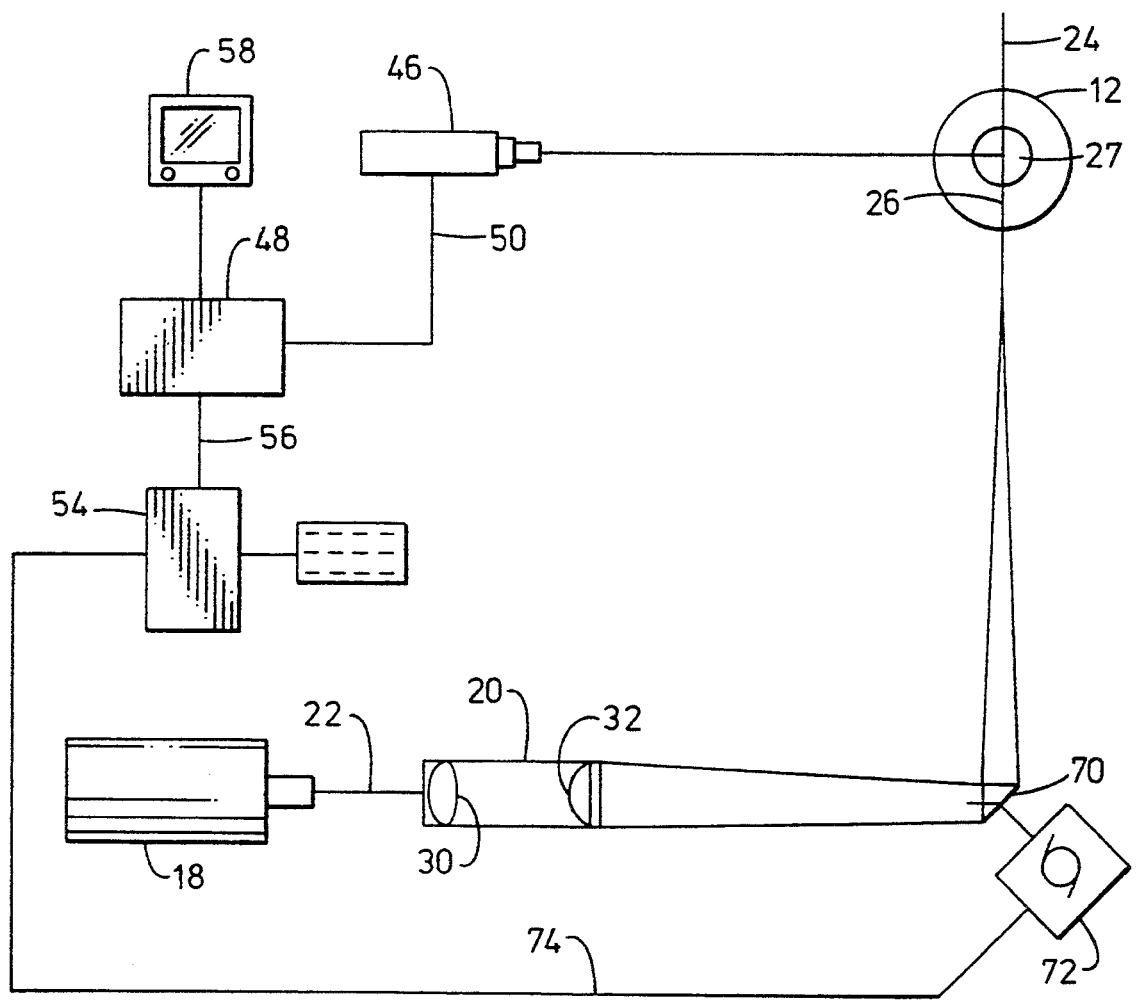
FIG. 2 is a schematic diagram of the powder stream analyzing device in accordance with another embodiment of the present invention.

In accordance with an alternative embodiment of the present invention, referring to FIG. 2, a pivotable mirror 70 may be used to advance or raster the light plane 24 through the powder stream 12 to illuminate a plurality of different cross-sections 26 of the powder stream 12 for analysis of the entire powder stream 12, including the interior portion 27. Images of each of the plurality of different cross-sections 26 may be generated by camera 46 and processed and stored by computers 48 and 54 during advancement of the light plane 24 through the powder stream 12 to reconstruct a three-dimensional representation of the powder stream 12. The pivotable mirror 70 may be pivoted by a small motor 72 which may be interconnected to the processing computer 54 by a suitable communications link 74 for control of the pivotable movement of the mirror 70.

Those skilled in the art will recognize that a plurality of light planes 24 may be generated simultaneously by using known optical components and projected through the powder stream 12 at different selected locations to illuminate different cross-sections 26 of the powder stream 12. In this respect, substantially the entire volume of the powder stream 12 may be observed and analyzed without having to step or raster a single light plane 24 through the powder stream 12. One means for generating a plurality of light planes 24 would be to provide multiple combinations of paired light sources 18 and line generator means 20. Another means for forming a plurality of light planes 24 would be to provide an optical component 75, such as a series of beam splitters, disposed between the line generator 20 and the powder stream 12 to split the light beam into multiple components or the optical component 75 may be disposed between the laser light source 18 and the line generator 20 to split the laser beam 22 into a plurality of beams.

Referring back to FIG. 1, while the present invention has been described with the plane 24 of light being projected substantially parallel to the direction of flow of the powder stream 12, those skilled in the art will recognize that the plane 24 of light may be projected at any angle relative to the direction of flow of the powder stream 12 including perpendicular to the powder stream flow as illustrated by the broken line 24' in FIG. 1. If the light plane 24' is oriented perpendicular to the flow of the powder stream 12 and perpendicular to the welding laser beam 28, a coaxial viewing device 76 may be used; such a device is described and claimed in co-pending U.S. patent application Ser. No. 07/826,496, entitled "Co-Axial Viewing Device for Lasers" by Vanon D. Pratt et al., which discloses and claims a laser welding apparatus which includes a viewing channel which allows real-time observation of the welding operation. This patent application is also assigned to the same assignee as the present application and is incorporated herein by reference in its entirety. Briefly described, the co-axial viewing device 76 includes a ZnSe window 78 which is specifically coated to pass the laser welding beam 28 and permit viewing the laser welding operation via an optical path 80. A focusing assembly 82 is disposed in a viewing channel 84 intermediate the ZnSe window 78 and an imaging system 86 which may include constituents similar to camera 46, vision computer 48, computer processor and storage unit 54 and monitor 58. Thus, multiple images of the illuminated, horizontal cross-section 88 of the powder stream 12 may be generated and stored as the plane of light 24' is advanced or rastered along the powder stream 12 in the direction of flow of the powder stream.

In accordance with the present invention, if the powder stream 12 is observed and analyzed during a welding operation, the light source 18 and the imaging system 86 or camera 46 preferably operate at the same wavelength which is substantially different from the spectral emissions produced during the welding process and different from the wavelength of the laser welding apparatus 16 so that the spectral emissions produced during processing and the spectral emissions of the laser beam 28 will be essentially transparent to the viewing system 86 or camera 46 and will not mask or obscure the illuminated cross-section 26 or 88 of the powder stream 12.

Figure 3:
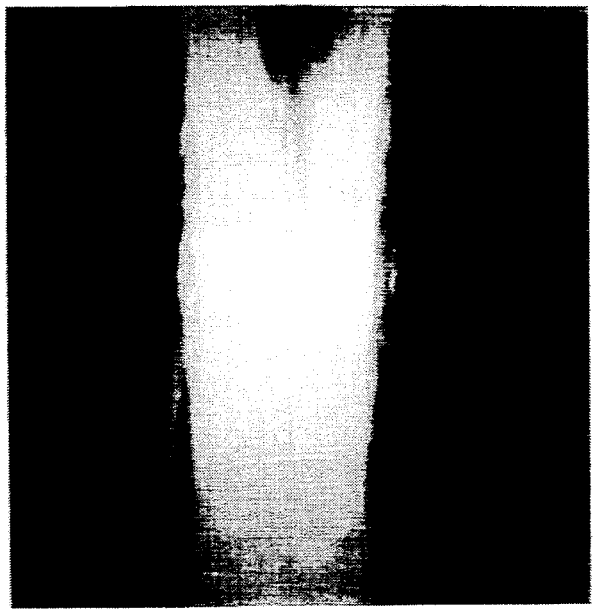
FIG. 3 is an image of a powder stream obtained using a prior art apparatus.

FIG. 3 is an image of a powder stream obtained using the prior art device and method of directing a white light on the powder stream. As can be seen, the interior portion of the powder stream is substantially obscured by the reflected light from the exterior portion of the powder stream.

Figure 4:
FIG. 4 is an image of a selected cross-section of the powder stream of FIG. 3 generated by the device of the present invention.

FIG. 4 is an image of a selected cross-section of the powder stream of FIG. 3 obtained by using the device of the present invention. As can be seen, the interior portion of the powder stream is clearly visible and the carrier gas flow rate can be approximately adjusted to provide the optimum shape or profile in accordance with the welding operation to be performed. In some welding operations, it may be desirable to have a nonuniform or asymmetrical powder stream. The device 10 of the present invention will permit observation and analysis of substantially any selected cross-section of a symmetrical or asymmetrical stream and a three-dimensional representation of the stream may be generated for analysis and to permit adjustment to the stream profile.

While the present invention has been described with respect to observing and analyzing a powder stream, such as a powder stream from a coaxial feed nozzle 14 of a laser welding apparatus 16 or the like, those skilled in the art will recognize that the present invention could also be used for the observation and analysis of any particle or fluid stream, such as those associated with plasma transfer arc welding, plasma spray, high velocity oxy fuel (HVOF), paint spraying systems, and other particle or fluid spraying systems. Additionally, those skilled in the art will recognize that other devices and methods may be used as well to generate the line of light 23 and the combination of the light source 18 and the line generator arrangement 20 are merely exemplary thereof. Thus, it will be readily understood by those skilled in the art that the present invention is not limited to the specific embodiments described and illustrated herein. Different embodiments and adaptations besides those shown herein and described as well as many variations, modifications and equivalent arrangements will now be apparent or will be reasonably suggested by the foregoing specification and drawings, without departing from the substance or scope of the invention. While the present invention has been described herein in detail in relation to its preferred embodiments, it is to be understood that this disclosure is only illustrative and exemplary of the present invention and is made merely for purposes of providing a full and enabling disclosure of the invention. Accordingly, it is intended that the invention be limited only by the spirit and scope of the claims appended hereto.

What is claimed is:

1. A method for analyzing and adjusting the shape of a stream of material, wherein the stream of material is a powder stream which flows coaxially about a laser beam operable at a first wavelength and usable for welding, the method comprising the steps of:
    (a) generating a plane of light;
    (b) projecting the plane of light through the stream to illuminate a selected cross-section of the stream;
    (c) observing and analyzing the shape of the stream at the selected cross-section from a location at an angle relative to said plane of light; and
    (d) detecting said illuminated, selected stream cross-section using a detector means and generating an image thereof, said light source and said detector means operating at a second wavelength which is substantially different from said first wavelength and different from spectral emissions created during a laser welding operation to permit observation and analysis of the powder stream during the laser welding operation.

2. The method of claim 1, further comprising the steps of adjusting a flow rate of the stream to provide a desired cross-sectional shape of the stream.

3. The method of claim 1, wherein the stream is a stream of particles carried by a carrier gas and said method further comprises the step of adjusting a flow rate of the carrier gas to provide a desired cross-sectional shape of the stream.

4. The method of claim 1, further comprising the step of moving the plane of light through the stream to illuminate a plurality of different cross-sections of the stream.

5. The method of claim 1, further comprising the step of generating an image of each of the plurality of different stream cross-sections as the plane of light is moved through the stream.

6. The method of claim 5, further comprising the step of digitizing and storing each of the images of the different stream cross-sections to generate a three-dimensional representation of the stream for analysis.

7. A device for observing and analyzing a stream of material, wherein the stream of material is a powder stream which flows coaxially about a laser beam operable at a first wavelength and usable for welding, the device comprising:
a laser light source for generating a beam of light;
a focusing lens disposed in a optical path between said laser source and the stream;
a plano-cylindrical lens of a selected focal length disposed in said optical path between said focusing lens and the stream, said focusing lens and said plano-cylindrical lens converting said beam of light to a plane of light and projecting said plane of light through the stream to illuminate a selected cross-section of the stream for observation and analysis of a profile of the stream from a location at an angle relative to said plane of light; and
detector means for detecting said illuminated, selected powder stream cross-section and for generating an image thereof, said laser light source and said detector means operating at a second wavelength which is substantially different from said first wavelength and different from spectral emissions created during a laser welding operation to permit observation and analysis of the powder stream during the laser welding operation.

8. The device of claim 7, wherein said laser light source generates a beam of visible light.

9. The device of claim 7, further comprising means for generating an image of said illuminated, selected stream cross-section.

10. The device of claim 7, further comprising means for moving said plane of light through the stream to illuminate a plurality of different cross-sections of the stream.

11. The device of claim 7, wherein said detector means comprises a means coaxial with said laser beam for observing the powder stream and the welding operation.

12. The device of claim 7, further comprising means for generating a plurality of light planes each projected through the stream at different locations to illuminate different selected cross-sections.

13. The device of claim 10, further comprising means for generating an image of each of said plurality of different stream cross-sections as said plane of light is moved through said stream.

14. The device of claim 13, further comprising computer means for digitizing and storing each of said images of said different stream cross-sections to generate a three-dimensional representation of the stream for analysis thereof.

15. A device for observing and analyzing a stream of material, wherein the stream of material is a powder stream which flows coaxially about a laser beam operable at a first wavelength and usable for welding, the device comprising:
a high intensity light source generating a beam of light;
means for converting said beam of light to a plane of high intensity light;
means for projecting said plane of high intensity light through the stream to illuminate a selected cross-section of the stream for observation and analysis of a profile of the stream from a location at an angle relative to said plane of light; and
detector means for detecting said illuminated, selected stream cross-section and for generating an image thereof, said light source and said detector means operating at a second wavelength which is substantially different from said first wavelength and different from spectral emissions created during a laser welding operation to permit observation and analysis of the powder stream during the laser welding operation.

16. The device of claim 15, further comprising means for generating an image of said illuminated, selected stream cross-section.

17. The device of claim 15, wherein said detector means comprises a means coaxial with said laser beam for observing the powder stream and the welding operation.

18. The device of claim 15, further comprising means for generating a plurality of light planes each projected through the stream at different locations to illuminate different selected cross-sections.

19. The device of claim 15, wherein the stream of material is a fluid.

20. The device of claim 15, wherein said light source is a visible light source.

21. The device of claim 20, wherein said light source is a laser.

22. The device of claim 15, further comprising means for moving said plane of light through the stream to illuminate a plurality of different cross-sections of the stream.

23. The device of claim 22, further comprising means for generating an image of each of said plurality of different stream cross-sections as said plane of light is moved through said stream.

24. The device of claim 23, further comprising computer means for digitizing and storing each of said images of said different stream cross-sections to generate a three-dimensional representation of the stream for analysis thereof.

* * * * *